United States Patent

Clerici et al.

[11] Patent Number: 5,817,842
[45] Date of Patent: Oct. 6, 1998

[54] PROCESS FOR THE PREPARATION OF EPOXIDES FROM OLEFINS

[75] Inventors: Mario Gabriele Clerici, S. Donato Milanese; Alberto de Angelis, Legnano; Patrizia Ingallina, S. Donato Milanese, all of Italy

[73] Assignee: Enichem S.p.A., Milan, Italy

[21] Appl. No.: 890,679

[22] Filed: Jul. 9, 1997

[30] Foreign Application Priority Data

Jul. 19, 1996 [IT] Italy .............................. MI96A 001500

[51] Int. Cl.$^6$ .................................. C07D 301/12
[52] U.S. Cl. ......................... 549/531; 546/340; 549/523; 502/62; 502/DIG. 22
[58] Field of Search .................................... 549/523, 531; 502/62, DIG. 22; 546/340

[56] References Cited

U.S. PATENT DOCUMENTS

| | | | |
|---|---|---|---|
| 4,824,976 | 4/1989 | Clerici et al. | 549/531 |
| 4,937,216 | 6/1990 | Clerici et al. | 502/62 |
| 5,214,168 | 5/1993 | Zajacek et al. | 549/531 |
| 5,221,795 | 6/1993 | Clerici et al. | 549/531 |
| 5,252,758 | 10/1993 | Clerici et al. | 549/531 |
| 5,463,090 | 10/1995 | Rodriguez et al. | 549/531 |

FOREIGN PATENT DOCUMENTS

| | | |
|---|---|---|
| 0 526 945 | 2/1993 | European Pat. Off. . |
| 0 549 013 | 6/1993 | European Pat. Off. . |

*Primary Examiner*—Zinna Northington Davis
*Attorney, Agent, or Firm*—Oblon, Spivak, McClelland, Maier & Neustadt, P.C.

[57] ABSTRACT

Process for the epoxidation of olefins with oxygen and/or air and a redox system, in the presence of titanium silicalite, characterized in that the redox system is selected from:

1) quinone/hydroquinone derivatives having the general formula (Ia) and (Ib)

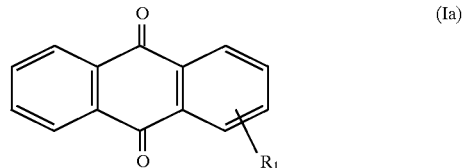

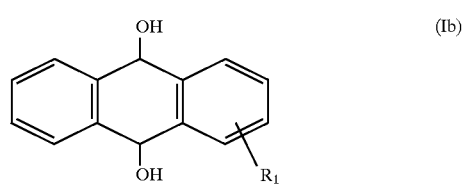

2) acetophenone/1-phenyl ethanol derivatives having the general formula (IIa) and (IIb)

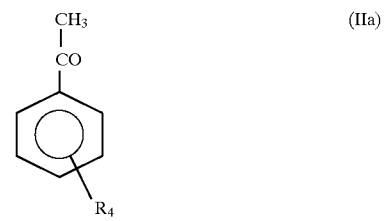

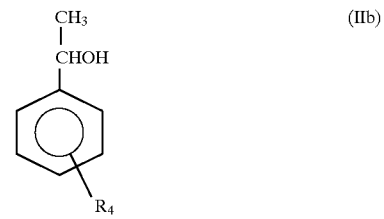

8 Claims, No Drawings

PROCESS FOR THE PREPARATION OF EPOXIDES FROM OLEFINS

The present invention relates to a process for the preparation of expoxides from olefins, particularly propylene oxide from propylene.

More specifically, the present invention relates to an integrated process for the preparation of epoxides in which an oxidable substrate, selected from a derivative of benzyl alcohol and a derivative of anthrahydroquinone, is oxidated with molecular oxygen to give a reaction product which epoxidates an olefin, the above epoxidation being catalyzed by a titanium silicalite.

The regeneration of the oxidated substrate, selected from a derivative of anthraquinone and benzophenone, is carried out with hydrogen and the substrate thus regenerated is sent back to the oxidation step.

One of the methods which has been developed for the preparation of epoxides involves the use of catalysts belonging to the group of Titanium-silicalites to catalyze the oxidation of olefins with hydrogen peroxide. The above methods are described for example in U.S. Pat. No. 4,824,979 and U.S. Pat. No. 4,833,260.

The prior art relating to epoxidation catalyzed by titanium-silicalite discloses that it is preferable to use solutions of hydrogen peroxide which do not contain large quantities of water and recommends the use of an organic solvent as epoxidation medium.

In fact EP A-526 945 describes a process for producing epoxides in which the hydrogen peroxide is generated in situ by the reaction of oxygen or air with a redox system consisting of alkyl-substituted anthraquinone, in the presence of the olefin to be epoxidated and, as catalyst, a titanium silicalite. The system described in EP A-526 945 involves the use of a particular solvent mixture consisting of one or more aromatic compounds, one or more high-boiling polar organic compounds and an alcohol with a low molecular weight. This process has the disadvantage of using a rather complicated mixture of solvents.

EP A-549 013 describes a process for the epoxidation of olefins with hydrogen peroxide in the presence of titanium silicalite, in which a water-alcohol mixture is used to extract the hydrogen peroxide produced in a redox process with alkyl-substituted anthraquinone. With respect to the other processes, this process however requires an additional step which consists in the extraction of the hydrogen peroxide produced.

U.S. Pat. No. 5,463,090 describes an integrated process for the production of epoxides which involves the use, again in the presence of titanium silicalite as catalyst, of alkylammonium salts of anthraquinone sulfonates in hydroalcohol mixtures. This process, although claiming the advantage of a high solubility of the anthraquinone derivatives in the water-alcohol mixtures, does not support this advantage with any experimental proof.

A process has now been found for the epoxidation of olefins which overcomes the disadvantages mentioned above.

In accordance with this, the present invention relates to a process for the epoxidation of olefins with oxygen and/or air and a redox system, in the presence of titanium silicalite, characterized in that the redox system is selected from:
1) quinone/hydroquinone derivatives having the general formula (Ia) and (Ib)

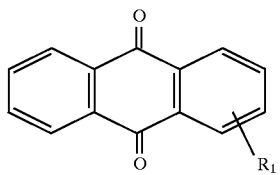

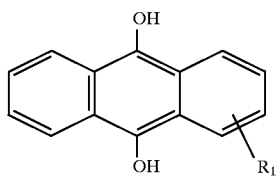

wherein $R_1$ is selected from (a) $-(-CH_2-)_n-N^+(R_2)_3$; (b) $-(-CH_2-)_n-CO_2^-N^+(R_3)_4$; $-(-CH_2-)_n-CO_2^-M^+$ 2) derivative of acetophenone/1-phenyl ethanol having the general formula (IIa) and (IIb)

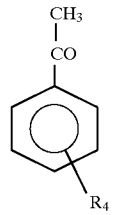

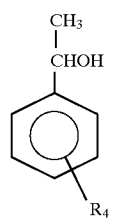

wherein $R_4$ is a monofunctional radical selected from those having the general formula $-(-CH_2-)_n-N^+(R_5)_3$, $-(-CH_2-)_n-SO_3^-N^+(R_6)_4$, $-(-CH_2-)_n-CO_2^-N^+(R_7)_4$, $-(-CH_2-)_n-CO_2^{-M+}$;

the number $R_1$ and $R_4$ being from 1 to 4, preferably from 1 to 2;

$R_2$, $R_3$, $R_5$, $R_6$ and $R_7$, the same or different, are monofunctional hydrocarbon radicals selected from $C_1-C_6$ alkyl, alkylaryl, aryl, arylalkyl; or two R groups, jointly, are equal to $-(-CH-)_5-$ thus giving rise to, together with nitrogen, a pyridinium;

n can be zero or an integer from 1 to 10, and is preferably from 0 to 3;

M is an alkaline metal, preferably sodium.

In one embodiment, the process of the present invention is an integrated process for producing epoxides, particularly propylene oxide, which comprises the following steps:

(a) reaction of the anthrahydroquinone derivative having general formula (Ib) or hydroxyl derivative having general formula (IIb) with molecular oxygen, to give an oxidation product essentially consisting of hydrogen peroxide and the anthraquinone derivative having general formula (Ia) or ketone derivative having general formula (IIa);

(b) putting the oxidation product obtained in step (a) in contact with an ethylenically unsaturated substrate, preferably propylene, and a catalytically efficient quantity of a titanium silicalite, to give a reaction mixture essentially containing the epoxide and the derivative (Ia) or (IIa);

(c) separating the epoxide and the titanium silicalite from the derivative having general formula (Ia) or (IIa);

(d) reacting the derivative (Ia) or (IIa) with hydrogen in the presence of a hydrogenation catalyst containing a transition metal thus converting the derivative (Ia) or (IIa) into the corresponding derivatives (Ib) or (IIb);

(e) recycling to step (a) the derivative (Ib) or (IIb) obtained in step (d).

In another embodiment, the process of the present invention is an integrated process for producing epoxides, particularly propylene oxide, which comprises the following steps:

(a) reaction of the anthrahydroquinone derivative having general formula (Ib) or hydroxyl derivative having general formula (IIb) with molecular oxygen and an ethylenically unsaturated substrate, preferably propylene, and a catalytically efficient quantity of a titanium silicalite, to give a mixture which comprises the epoxide and anthraquinone derivative (Ia) or ketone derivative (IIa);

(b) separating the epoxide and the titanium silicalite from the compound having general formula (Ia) or (IIa);

(c) reacting the compound having general formula (Ia) or (IIa) separated in step (b) with hydrogen in the presence of a transition metal thus converting the derivative (Ia) or (IIa) into the corresponding derivatives (Ib) or (IIb);

(d) recycling to step (a) the derivative (Ib) or (IIb) obtained in step (c).

The quinone compounds having general formula (Ia) have, with reference to anthraquinone, from 1 to 4, preferably from 1 to 2
—H atoms substituted with groups selected from —(—$CH_2$—)$_n$—$N^+(R_2)_3$; —(—$CH_2$—)$_n$—$CO_2^-N^+(R_3)_4$; —(—$CH_2$—)$_n$—$CO_2^-M^+$, wherein n, $R_2$ and $R_3$ have the meaning defined above.

The acetophenone derivatives having general formula (IIa) have, with reference to acetophenone, from 1 to 4, preferably from 1 to 2, aromatic hydrogens substituted by groups selected from —(—$CH_2$—)$_n$—$N^+(R_5)_3$, —(—$CH_2$—)$_n$—$SO_3^-N^+(R_6)_4$, —(—$CH_2$—)$_n$—$CO_2^-N^+(R_7)_4$, —(—$CH_2$—)$_n$—$CO_2^-M^+$, wherein n, $R_5$, $R_6$, $R_7$ and M have the meaning defined above.

As the possible solvent which can be used in the process of the present invention consists of mixtures of water/lower alcohols, preferably methanol and/or ethanol, it is possible, by varying the number of substituents (from 1 to 4) and the type of $R_2$, $R_3$, $R_5$, $R_6$ and $R_7$ (which we shall simply call R), to optimize the solubility of the redox couple with variations in the water/alcohol ratio.

In this way, with the same R type, the solubility in water increases with an increase in the number of substituents. On the contrary, with the same number of substituents, the solubility in water decreases with the increase in the number of carbon atoms present in R.

The compounds having general formula (Ia) and (IIa) can obviously have hydrogen atoms substituted with groups which are non-reactive towards the reaction environment, in particular alkyl groups.

Typical compounds having general formula (Ia) are 2-methylpyridine-9,10-anthraquinone halides, preferably bromide and chloride, 2-metyl-N-trimethyl-9,10-anthraquinone halides, preferably bromide and chloride, 9,10-anthraquinone-2-carboxylates of tetraalkylammonium or alkaline metals, preferably tetramethylammonium or Sodium, 9,10-anthraquinone-2-acetates of tetraalkylammonium or alkaline metals, preferably tetramethylammonium or sodium.

Typical compounds having general formula (IIa) are meta or para acetophenonesulfonates of tetraalkylammonium, preferably tetramethylammonium, para or meta acetophenone-methyl-N-dimethylbutylammonium halides, preferably chlorides and bromides, para and meta acetophenonemethylpyridine halides, preferably chlorides and bromides.

The above compounds having general formula (Ia) can be prepared by the halogenation, preferably bromination and chlorination, of 2-methyl-9,10-anthraquinone and subsequent reaction with an amine, or oxidation of suitable precursors, such as alkyl derivatives or alcohols.

The above compounds having general formula (IIa) are prepared by the sulfonation of acetophenone or by the acylation of a benzylamine.

The process of the present invention preferably uses a solvent, even more preferably a protic polar solvent.

Suitable examples of protic polar solvents are water and $C_1$–$C_6$ alcohols (for example methanol, ethanol, ter-butylic alcohol). The solvent, or solvent mixture, is preferably inert under the oxidation, epoxidation and hydrdogenation conditions. In a preferred embodiment of the present invention, the volume of solvent used is minimized with respect to the quantity of redox system (I) or (II), but is still sufficient to completely dissolve or solubilize the above redox system. In this way it is possible to maximize the concentration of hydrogen peroxide in the oxidation mixture and consequently maximize the total productivity of the system.

The reaction with molecular oxygen can be carried out under similar conditions to those used in conventional processes for the production of hydrogen peroxide in the presence of anthrahydroquinone derivatives. Air, pure oxygen or pure oxygen diluted with another gas, for example nitrogen, can be used as molecular oxygen source.

Optimum reaction rates and selectivities can generally be obtained operating at temperatures of between 0° C. and 100° C., preferably between 20° C. and 60° C., and a partial oxygen pressure of between 0.5 and 100 bars, preferably from 1 to 10 bars.

The oxidation is preferably carried out in liquid phase with molecular oxygen which is sparged or introduced in any other way into the liquid phase containing the dissolved compound having general formula (I) or (II).

In order to minimize any possible side reactions, the contact time of the compound having general formula (Ib) or (IIb) with the oxygen is preferably limited, and is typically less than 90 minutes. It is generally preferable to obtain a conversion of the compound having general formula (Ib) or (IIb) of between 30% and 90%. The optimum contact time depends, among other factors, on the partial oxygen pressure, the temperature, the reactivity of the derivative having general formula (Ib) or (IIb). As far as the quantity of oxygen is concerned, this should preferably be such as to avoid the explosivity range although maintaining an equimolar ratio or slight molar excess with respect to the compound having general formula (Ib) or (IIb).

The oxidated mixture obtained at the end of the oxidation process essentially consists of hydrogen peroxide, the compound having general formula (Ia) or (IIa) corresponding to the initial compounds (Ib) or (IIb), the non-reacted compounds (Ib) or (IIb) and the possible solvent. During the above oxidation step a concentration of hydrogen peroxide of 0.5% by weight or more can be obtained.

In the oxidation step of the process of the present invention, the mixture of oxidated product is put in contact with an ethylenically unsaturated substrate and a catalytically efficient quantity of titanium silicalite, preferably at a temperature of between 0° C. and 120° C., more preferably from 30° C. to 60° C., thus converting the substrate to the desired epoxide.

Although the product of the oxidation step can be purified before the epoxidation step, an important advantage of the process of the present invention is that this pretreatment is not necessary for obtaining satisfactory yields of epoxide.

In another form of embodiment, the oxidation step and the epoxidation step are carried out contemporaneously generating hydrogen peroxide in situ. In this case the compound having general formula (Ib) or (IIb) is reacted with molecular oxygen and the ethylenically unsaturated substrate in the presence of titanium silicalite, preferably at a temperature of between 0° C. and 120° C., more preferably from 10° C. to 80° C., even more preferably from 30° C. to 60° C., to form a mixture of epoxidation product comprising the compound having general formula (Ia) or (IIa) and the desired epoxide.

The ethylenically unsaturated compound to be subjected to epoxidation is preferably an organic compound having from 2 to 16 carbon atoms and at least one ethylenically unsaturated functional group (i.e. a double carbon-carbon bond) and can be a cyclic, branched or linear aliphatic olefin. More than one double bond can be present in the olefin, and dienes, trienes and other polyunsaturated substrates can therefore be used.

Typical examples of olefins which can be used in the process of the present invention are ethylene, propylene, butenes, butadiene, pentenes, isoprene, 1-hexene, 3-hexene, 1-heptene, 1-octene, diisobutylene, 1-nonene, trimers and tetramers of propylene, cyclopentene, cyclohexene, cycloheptene, cyclooctene, cyclooctadiene, dicyclopentadiene, methylenecyclopropane, methylenecyclopentane, methylenecyclohexane, vinylcyclohexane.

Mixtures of olefins can also be subjected to epoxidation, and the resulting epoxides can be used as such or separated into the different epoxides.

The process of the present invention is particularly suitable for the epoxidation of $C_2$–$C_{16}$ olefins having the general formula

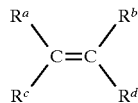

wherein $R^a$, $R^b$, $R^c$ and $R^d$ wherein n, $R_2$ and $R_3$, the same or different, are selected from H and $C_1$–$C_8$ alkyl groups, so that the total number of carbon atoms of the olefin is not higher than 16.

The process of the present invention is also convenient for epoxidating ethylenically unsaturated substrates containing functional groups different from alkyl groups. For example the double carbon-carbon bond can be substituted with groups such as —COOH, —COOR, —CN, or —OR, wherein R is an alkyl, cycloalkyl, aryl or aralkyl substituent.

The radicals $R^a$, $R^b$, $R^c$ and $R^d$ in the above formula can contain other functional groups selected from the aryl, aralkyl, halo, nitro, sulfonic, cyano, carbonyl (i.e. ketones or aldehydes), hydroxyl, carboxyl (i.e. acids or esters), ether group. Examples of ethylenically unsaturated compounds of this type comprise allyl alcohol, styrene, allyl chloride, allyl methyl ether, allyl phenyl ether, methyl methacrylate, acrylic acid, methyl acrylate, stilbene.

Although the molar ratio between substrate and hydrogen peroxide is not critical, it is generally preferable, mainly for practical reasons, to use a molar ratio of between 10/1 and 1/10.

The titanium silicalites used as catalysts in the epoxidation step comprise the group of crystalline zeolites where the Titanium partly substitutes Silicon and Aluminum atoms in the crystalline lattice of a silicalite or alumosilicalite. Titanium silicalites are characterized by their insolubility in organic mediums. Titanium silicalites are well-known in literature and are described for example in U.S. Pat. No. 4,410,501, U.S. Pat. No. 4,824,976, U.S. Pat. No. 4,666,692, U.S. Pat. No. 4,656,016, U.S. Pat. No. 4,859,785.

Particularly preferred are titanium silicalites belonging to the "TS-1" group, having an MFI topology analogous to that of ZSM-5 alumosilicate zeolites, TS-2 group, (having a MEL topology analogous to that of ZSM-11 aluminosilicate zeolites) and TS-3 group described in BE-A-1.001.038.

Molecular sieves containing Titanium having a structure isomorphous with beta zeolite can also be used, such as those described in PCT Publication Nr. WO 94/02245, U.S. Pat. No. 4,892,720, U.S. Pat. No. 5,098,687, U.S. Pat. No. 5,233,097 and U.S. Pat. No. 5,271,761. Preferably the titanium silicalite does not contain atoms different from Oxygen, Titanium and Silicon in the crystalline cross-linking, even if minimum quantities of Boron, Iron, Aluminum, Phosphorous can be present.

When $Al^{3+}$ ions are present in the structure of the titanium silicalite, a suitable quantity of a basic salt (alkaline or earth-alkaline metal or ammonium) is added to the reaction solution to neutralize the acidity of the catalyst and prevent the hydrolysis of the epoxide.

The addition of the basic substance can be carried out, in smaller quantities however, even when the titanium silicalite is without $Al^{3+}$.

The titanium silicalites which can be used in the process of the present invention typically have a composition, as described in EP-A-100.119, corresponding to the empirical formula $xTiO_2.(1-x)SiO_2$, wherein x is between 0.0001 and 0.04. The value of x is more preferably from 0.01 to 0.025.

The quantity of catalyst used is not critical, but should be sufficient to complete the desired epoxidation reaction within an acceptable time range.

The ideal quantity of catalyst depends on various parameters, such as reaction temperature, reactivity of the substrate, its concentration, the concentration of hydrogen peroxide, the type and composition of solvent used, the catalytic activity and type of reactor or reaction system used. In a batch or slurry type reactor, for example, the ideal quantity of catalyst is influenced by the flow rate of the reagents through the fixed bed. The overall concentration of Titanium in the reaction system is generally from 10 to 10,000 ppm.

The catalyst can be used in the form of powder, pellets, microspheres, extruded, monolytic or other convenient physical forms. It can be advantageous to use a ligand (co-gel) or carrier combined with the titanium silicalite. The supported or bound catalysts can be prepared with the methods known in the art.

The following examples provide a better understanding of the present invention ; however they are not to be intended as limiting the scope thereof. As a matter of fact, some other compounds falling under the general formulae $I_a$, $I_b$, $II_a$ and $II_b$, particularly the ones listed in page 8, may promote the same results as those described in the examples when used according to the teaching underlined throughout the specification.

EXAMPLE 1

0.86 grams (2.6 mmoles) of 2-methylpyridine-9,10-anthraquinone bromide, 20 ml of a solvent consisting of MeOH and $H_2O$ (1:1 by volume) and 0.10 grams of Pd/C 5%, are charged into a 70 ml pyrex glass pressure-resistant reactor.

The reactor is then charged with 3 bars of hydrogen and heated to 40° C. After about 2 hours under vigorous stirring and after a pressure drop of about 1.3 bars, the hydrogen consumption is stopped. The suspension is then filtered under a nitrogen atmosphere and an orange-brown coloured solution is obtained.

The above solution is then charged into a 250 ml pyrex glass pressure-resistant reactor together with 0.052 grams of Titanium silicalite prepared according to example 1 of U.S. Pat. No. 4,410,501 and a certain quantity of methyl-terbutyl ether (as chromatographic standard). The reactor is then pressurized with 1 bar of propylene and a strong excess of air. The mixture is left to react at 40° C. for about 90 minutes. According to chromatographic analysis propylene oxide is obtained with a yield equal to 71.3% with respect to the anthraquinone charged at the be inning.

EXAMPLE 2

To an autoclave of Pyrex glass, of 250 ml of capacity, 1 g (2.5 mmol) of 2-Anthraquinonylmethylpiperidinium bromide dissolved in 60 ml of a solvent based on methanol:water(1:1 by volume) and 0,25 g of 5 wt % Pt over carbon are charged.

The autoclave is then charged with 3 bars of hydrogen and the reaction is carried out at ambient temperature under vigorous stirring. After that 1.2 mmoles of hydrogen are consumed (about 20 minutes), the reaction is stopped and the resulting suspension is filtered under an inert atmosphere in a round bottom flask.

The above said solution is oxidized in the presence of air and hydrogen peroxide is obtained.

EXAMPLE 3

To an autoclave of Pyrex glass, of 250 ml of capacity, 1 g (2.5 mmol) of 2-Anthraquinonylmethylpiperidinium bromide dissolved in 60 ml of a solvent based on methanol:water(1:1 by volume) and 0.25 g of 5 wt % Pt over carbon are charged.

The autoclave is then charged with 3 bars of hydrogen and the reaction is carried out at ambient temperature under vigorous stirring. After that 1.2 mmoles of hydrogen are consumed (about 20 minutes), the reaction is stopped and the resulting suspension is filtered under an inert atmosphere.

To a Pyrex glass autoclave of 250 ml of capacity, the above said solution is charged together with 0.5 g of titanium silicalite (0.30 wt %), 1.5 bars of propylene, 1.5 bars of air and a known amount of methyl tert-butyl ether (internal gas-chromatographic standard) are charged.

The reaction is carried out at ambient temperature and propylene oxide is obtained.

We claim:

1. A process for the epoxidation of an olefin with oxygen and/or air and a redox system, in the presence of titanium silicalite, wherein the redox system is:

a compound of acetophenone/1-phenyl ethanol having formula (Ia) or (IIb)

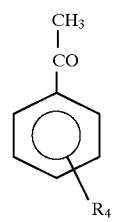

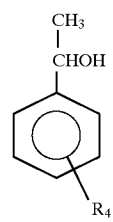

wherein $R_4$ is a monofunctional radical selected from the group consisting of those having the formula:

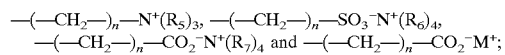

the number of $R_4$ being from 1 to 4;

$R_5$, $R_6$ and $R_7$, the same or different, are monofunctional hydrocarbon radicals selected from the group consisting of $C_1$–$C_6$ alkyl, alkylaryl, aryl and arylalkyl; or two R groups, jointly, are equal to —(CH—)$_5$— thus giving rise, together with a nitrogen atom, to a pyridinium;

n can be zero or an integer from 1 to 10; and

M is an alkaline metal.

2. The process according to claim 1, wherein the number of $R_4$ is from 1 to 2.

3. The process according to claim 1, wherein n is zero or an integer from 1 to 3.

4. The process according to claim 1, wherein the compounds having formula (IIa) are selected from the group consisting of:

a para or meta acetophenone-methyl-N-dimethyl-butylammonium halide, a meta or para acetophenonesulfonate of tetraalkylammonium and a para or meta acetophenonemethylpyridine halide.

5. The integrated process for producing an epoxide according to claim 1, which comprises the following steps:

(a) reacting the hydroxyl compound having formula (IIb) with molecular oxygen, to give an oxidation product consisting essentially of hydrogen peroxide and a ketone compound having formula (IIa);

(b) putting the oxidation product obtained in step (a) in contact with an ethylenically unsaturated substrate and a catalytically efficient quantity of a titanium silicalite, to give a reaction mixture essentially containing the epoxide and compound (IIa);

(c) separating the epoxide and the titanium silicalite from the compound having formula (IIa);

(d) reacting the compound (IIa) with hydrogen in the presence of a hydrogenation catalyst containing a transition metal thus converting the compound (IIa) into compound (IIb);

(e) recycling to step (a) the compound (IIb) obtained in step (d).

6. The integrated process for producing an epoxide according to claim 1, which comprises the following steps:
- (a) reacting the hydroxyl compound having general formula (IIb) with molecular oxygen and an ethylenically unsaturated substrate, and a catalytically efficient quantity of a titanium silicalite, to give a mixture which comprises the epoxide and the ketone compound (IIa);
- (b) separating the epoxide and the titanium silicalite from the compound having formula (IIa);
- (c) reacting the compound having formula (IIa) separated in step (b) with hydrogen in the presence of a transition metal thus converting the compound (IIa) into compound (IIb);
- (d) recycling to step (a) the compound (IIb) obtained in step (c).

7. The process according to claim 1, wherein said alkaline metal is sodium.

8. The process according to claim 5, wherein said epoxide is propyleneoxide and said ethylenically unsaturated substrate is propylene.

* * * * *